(12) United States Patent
Pazenok et al.

(10) Patent No.: US 7,939,673 B2
(45) Date of Patent: May 10, 2011

(54) PROCESS FOR PREPARING 3-DIHALOMETHYL-PYRAZOLE-4-CARBOXYLIC ACID DERIVATIVES

(75) Inventors: Sergi Pazenok, Solingen (DE); Lui Norbert, Odenthal (DE); Arnd Neeff, Enneptal (DE)

(73) Assignee: Bayer CropScience AG, Monheim (DE)

( * ) Notice: Subject to any disclaimer, the term of this patent is extended or adjusted under 35 U.S.C. 154(b) by 148 days.

(21) Appl. No.: 12/438,732

(22) PCT Filed: Aug. 22, 2007

(86) PCT No.: PCT/EP2007/007377
§ 371 (c)(1),
(2), (4) Date: Feb. 25, 2009

(87) PCT Pub. No.: WO2008/022777
PCT Pub. Date: Feb. 28, 2008

(65) Prior Publication Data
US 2009/0326242 A1    Dec. 31, 2009

(30) Foreign Application Priority Data
Aug. 25, 2006 (DE) .......... 10 2006 039 909

(51) Int. Cl.
C07D 231/10    (2006.01)
C07C 229/00    (2006.01)
(52) U.S. Cl. .................... 548/374.1; 560/169
(58) Field of Classification Search ............... 548/374.1; 560/360
See application file for complete search history.

(56) References Cited

U.S. PATENT DOCUMENTS

| 5,401,869 A | 3/1995 | Kraus et al. |
| 5,489,624 A | 2/1996 | Kantner et al. |
| 6,706,911 B1 | 3/2004 | Lui et al. |
| 7,355,065 B2 | 4/2008 | Walter et al. |

FOREIGN PATENT DOCUMENTS

| WO | 03/074491 | 9/2003 |
| WO | 2005/042468 | 5/2005 |
| WO | 2006/045504 | 5/2006 |

OTHER PUBLICATIONS

International Search Report for Application PCT/EP2007/007377 dated Feb. 19, 2008 (6 pages).
Pashkevich, K. I. et al., "Reaction of 2-acetyl-substituted Polyfluorinated.beta.-keto Esters with Amines," Chemical Abstracts Service, Doc. XP-002469504, Columbus, OH, p. 1.
Dmowski, W., "Replacement of Sulfur by Fluorine," American Chemical Society, 1995, pp. 263-270.
Petrov, Viacheslav et al., "1,1,2,2-Tetrafluoroethyl-N,N-dimethylamine: A New Selective Fluorinating Agent," Journal of Fluorine Chemistry, No. 109, 2001, pp. 25-31.
Jones, Reuben G., "The Synthesis of Ethyl Ethoxymethyleneoxalacetate and Related Compounds," Journal of the American Chemical Society, vol. 73, 1951, pp. 3684-3686.
Rubinstein, Ian et al., "The Occurrence of Nuclear Methylated Steranes in a Shale," Journal of the Chemical Society, No. 24, 1975, pp. 958-960.
Rene, Loic et al., "A One Pot Synthesis of β-Cyanoenamines," Communications, May 1986, pp. 419-420.

*Primary Examiner* — Rebecca L Anderson
*Assistant Examiner* — Samantha L Shterengarts
(74) *Attorney, Agent, or Firm* — Baker Donelson Bearman, Caldwell & Berkowitz, PC

(57) ABSTRACT

The invention relates to a process for preparing 3-dihalomethylpyrazole-4-carboxylic acid derivatives of the formula (I) by reacting α-fluoroamines of the formula (III) in the presence of Lewis acids with acrylic acid derivatives of the formula (II) to give vinamidinium salts of the formula (IV) and the subsequent reaction thereof with hydrazines, and to the vinamidinium salts of the formula (IV) themselves.

11 Claims, No Drawings

US 7,939,673 B2

PROCESS FOR PREPARING 3-DIHALOMETHYL-PYRAZOLE-4-CARBOXYLIC ACID DERIVATIVES

CROSS REFERENCE TO RELATED APPLICATIONS

This application is a §371 National Stage Application of PCT/EP2007/007377 Aug. 22, 2007 which claims priority to German Application 10 2006 039 909.9 filed Aug. 25, 2006.

BACKGROUND OF THE INVENTION

1. Field of the Invention

The invention relates to a process for preparing 3-dihalomethylpyrazole-4-carboxylic acid derivatives of the formula (I) by reacting α-fluoroamines of the formula (III) in the presence of Lewis acids with acrylic acid derivatives of the formula (II) to give vinamidinium salts of the formula (IV) and the subsequent reaction thereof with hydrazines, and to the vinamidinium salts of the formula (IV) themselves.

2. Description of Related Art

3-Difluoromethylpyrazole-4-carboxylic esters, -carboxamides and -carbonitriles are important synthetic units for preparing active agrochemical ingredients, especially for preparing pyrazolylcarboxanilide fungicides.

WO-A-05 042 468 teaches a process for preparing 2-dihaloacyl-3-aminoacrylic esters by reacting acid halides with dialkylaminoacrylic esters, and the reaction thereof with hydrazine derivatives to give 3-dihalomethylpyrazole-4-carboxylic esters.

WO-A-03 051 820 teaches the preparation of 2-haloacyl-3-aminoacrylic esters by reacting N-substituted 3-aminoacrylic esters with haloalkylcarboxylic anhydrides and the subsequent reaction thereof with hydrazine derivatives to give 3-haloalkylpyrazole-4-carboxylic esters. The reaction to give the 3-haloalkylpyrazole-4-carboxylic esters proceeds unselectively at room temperature and therefore has to be performed at low temperatures (−80° C.).

WO-A-06 005 612 teaches a process for preparing ethyl 4,4-difluoro-3-oxobutyrate by reacting 2,2-difluoro-N-dialkylacetamide with acetic esters in the presence of bases. The ethyl 4,4-difluoro-3-oxobutyrate is subsequently, as described in JACS, 73, 3684 (1951), reacted with trimethyl orthoformate and acetic anhydride to give ethyl (2-ethoxymethylene)-4,4-difluoromethylacetoacetate, which, according to U.S. Pat. No. 5,489,624, can be converted with methylhydrazine to ethyl 3-difluoromethyl-1-methyl-4-pyrazolecarboxylate. The route described firstly includes a multitude of reaction steps, and, secondly, the 2,2-difluoro-N-dialkylacetamide used is not commercially available and can be obtained only in low yields of approx. 70% by fluorinating 2,2-dichloro-N-dialkylacetamide.

The processes described to date in the prior art have the disadvantage that the carbonyl halides, haloalkylcarboxylic anhydrides and haloacrylic esters used are expensive, cause corrosion problems and/or can be purified only with a high level of technical complexity.

SUMMARY OF THE INVENTION

It is therefore an object of the present invention to provide a simpler and more economically viable process for preparing 2-haloacyl-3-aminoacrylic ester derivatives, especially esters, nitriles and amides.

The object described above is achieved in accordance with the invention by a process for preparing 3-dihalomethylpyrazole-4-carboxylic acid derivatives of the formula (I)

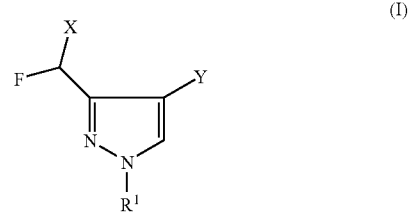

in which $R^1$ is selected from $C_{1-12}$-alkyl radicals, $C_{5-18}$-aryl or $C_{7-19}$-arylalkyl radicals, Y is selected from (C=O)$OR^6$, CN and (C=O)$NR^7R^8$, where $R^6$, $R^7$ and $R^8$ are each independently selected from $C_{1-12}$-alkyl radicals, $C_{5-18}$-aryl or $C_{7-19}$-arylalkyl radicals; and X is F, Cl or $CF_3$ by reacting α-fluoroamines of the formula (III)

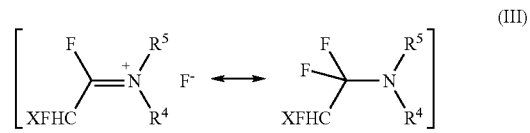

in which $R^4$ is selected from $C_{1-12}$-alkyl radicals, $C_{5-18}$-aryl or $C_{7-19}$-arylalkyl radicals, $R^5$, independently of $R^4$, is selected from $C_{1-12}$-alkyl radicals, $C_{5-18}$-aryl or $C_{7-19}$-arylalkyl radicals, and X is F, Cl or $CF_3$, in the presence of Lewis acids (Z) with acrylic acid derivatives of the formula (II)

in which

A is selected from O, S and $NR^3$,

Y is selected from (C=O)$OR^6$, CN and (C=O)$NR^7R^8$, where $R^6$, $R^7$ and $R^8$ are each independently selected from $C_{1-12}$-alkyl radicals, $C_{5-18}$-aryl or $C_{7-19}$-arylalkyl radicals; and $R^2$ and $R^3$ are each independently selected from $C_{1-12}$-alkyl radicals, $C_{5-18}$-aryl or $C_{7-19}$-aryl-alkyl radicals, —OR', —SR', —NR'$_2$, where R' may be a ($C_1$-$C_5$) alkyl radical, or $R^2$ and $R^3$, together with the nitrogen atom to which they are bonded, may form a five- or six-membered ring, and the subsequent reaction thereof with hydrazines of the general formula (V)

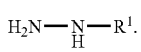   (V)

The present invention further relates to the vinamidinium salt of the formula (IV) formed as an intermediate in the process according to the invention

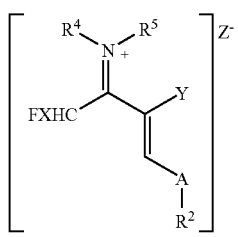   (IV)

in which
all radicals are as defined above.

Further embodiments of the present invention can be taken from the dependent claims and the description.

DETAILED DESCRIPTION OF A PREFERRED EMBODIMENT

The process according to the invention can be illustrated with reference to Scheme (I) which follows:

Scheme (I)

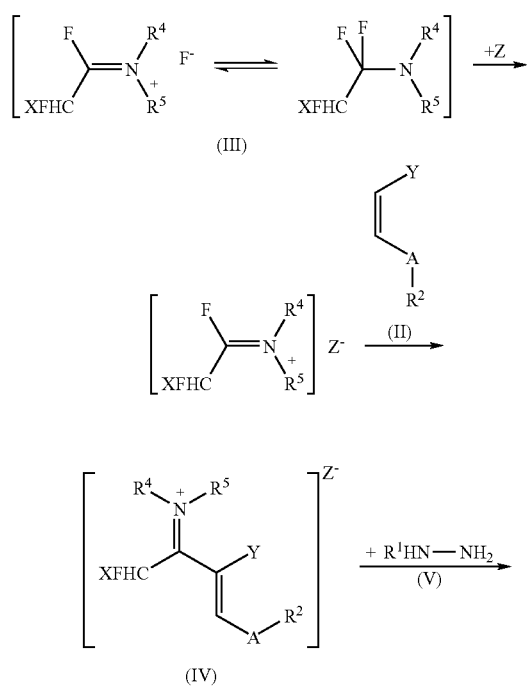

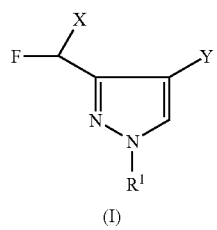   (I)

General Definitions

In connection with the present invention, the term halogens (X), unless defined otherwise, includes those elements which are selected from the group consisting of fluorine, chlorine, bromine and iodine, preference being given to fluorine, chlorine and bromine and particular preference to fluorine and chlorine.

Optionally substituted groups may be mono- or polysubstituted, and the substituents may be the same or different in the case of multiple substitutions.

In connection with the present invention, the —X group denotes a halogen atom which is selected from fluorine, chlorine, bromine and iodine, preferably fluorine, chlorine and bromine, more preferably from fluorine and chlorine.

Alkyl groups substituted by one or more halogen atoms (—X) are, for example, selected from trifluoromethyl ($CF_3$), difluoromethyl ($CHF_2$), $CF_3CH_2$, $ClCH_2$, $CF_3CCl_2$.

In connection with the present invention, unless defined differently, alkyl groups are linear, branched or cyclic hydrocarbon groups which may optionally have one, two or more single or double unsaturations or one, two or more heteroatoms which are selected from O, N, P and S. In addition, the inventive alkyl groups may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C═O)R') and amide groups (—CONR$_2$'), where R' may be hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_1$-$C_{12}$-alkyl encompasses the largest range defined herein for an alkyl group. Specifically, this definition includes, for example, the meanings of methyl, ethyl, n-, iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, unless defined differently, alkenyl groups are linear, branched or cyclic hydrocarbon groups which contain at least one single unsaturation (double bond) and may optionally have one, two or more single or double unsaturations or one, two or more heteroatoms which are selected from O, N, P and S. In addition, the inventive alkenyl groups may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C═O)R') and amide groups (—CONR$_2$'), where R' may be hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_2$-$C_{12}$-alkenyl encompasses the largest range defined herein for an alkenyl group. Specifically, this definition includes the meanings of vinyl; allyl (2-propenyl), isopropenyl (1-methylethenyl); but-1-enyl (crotyl), but-2- enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

In connection with the present invention, unless defined differently, alkynyl groups are linear, branched or cyclic hydrocarbon groups which contain at least one double unsaturation (triple bond) and may optionally have, one, two or more single or double unsaturations or one, two or more heteroatoms which are selected from O, N, P and S. In addition, the inventive alkynyl groups may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a linear, branched or cyclic $C_{1-12}$-alkyl group which may have one or more heteroatoms selected from N, O, P and S.

The definition $C_2$-$C_{12}$-alkynyl encompasses the largest range for an alkynyl group defined herein. Specifically, this definition encompasses, for example, the meanings of ethynyl (acetylenyl); prop-1-ynyl and prop-2-ynyl.

In connection with the present invention, unless defined differently, aryl groups are aromatic hydrocarbon groups which may have one, two or more heteroatoms which are selected from O, N, P and S and may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl-(—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_{5-18}$-aryl encompasses the largest range for an aryl group having 5 to 18 atoms defined herein. Specifically, this definition encompasses, for example, the meanings of cyclopentadienyl, phenyl, cycloheptatrienyl, cyclooctatetraenyl, naphthyl and anthracenyl.

In connection with the present invention, unless defined differently, arylalkyl groups (aralkyl groups) are alkyl groups which are substituted by aryl groups and may have a $C_{1-8}$-alkylene chain and may be substituted in the aryl skeleton or the alkylene chain by one or more heteroatoms which are selected from O, N, P and S and may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_{7-19}$-aralkyl group encompasses the largest range for an arylalkyl group having a total of 7 to 19 atoms in the skeleton and alkylene chain defined herein. Specifically, this definition encompasses, for example, the meanings of benzyl and phenylethyl.

In connection with the present invention, unless defined differently, alkylaryl groups (alkaryl groups) are aryl groups which are substituted by alkyl groups and may have a $C_{1-8}$-alkylene chain and may be substituted in the aryl skeleton or the alkylene chain by one or more heteroatoms which are selected from O, N, P and S and may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_{7-19}$-alkylaryl group encompasses the largest range for an alkylaryl group having a total of 7 to 19 atoms in skeleton and alkylene chain defined here. Specifically, this definition encompasses, for example, the meanings of tolyl, 2,3-, 2,4-, 2,5-, 2,6-, 3,4- or 3,5-dimethylphenyl.

The alkyl, alkenyl, alkynyl, aryl, alkaryl and aralkyl groups may additionally have one or more heteroatoms which—unless defined differently—are selected from N, O, P and S. In this case, the heteroatoms replace the numbered carbon atoms. Not included are those combinations which contravene the laws of nature and which would therefore have been ruled out by the person skilled in the art on the basis of his or her technical knowledge. For example, ring structures with three or more adjacent oxygen atoms are ruled out.

The inventive compounds may optionally be present as mixtures of different possible isomeric forms, especially of stereoisomers, for example E and Z, threo and erythro, and also optical isomers, but optionally also of tautomers. Both the E and the Z isomers, and also the threo and erythro, and the optical isomers, any mixtures of these isomers, and the possible tautomeric forms are disclosed and claimed.

Acrylic Acid Derivatives

The acrylic acid derivatives used in accordance with the present invention are compounds of the general formula (II).

(II)

In this compound, A is selected from O, S and NR$^3$, and the R$^2$ and R$^3$ radicals are each independently selected from $C_{1-12}$-alkyl radicals, $C_{5-18}$-aryl, $C_{7-19}$-arylalkyl radicals, alkoxy groups (—OR'), mercapto groups (—SR'), amino groups (—NR'$_2$), where R' may be a $C_{1-5}$-alkyl radical.

Alternatively, R$^2$ and R$^3$, together with the nitrogen atom to which they are bonded, form a five- or six-membered ring.

The R$^2$ and R$^3$ radicals are preferably each independently selected from $C_{2-8}$-alkyl radicals, O—($C_{2-6}$-alkyl), S—($C_{2-6}$-alkyl), N($C_{2-6}$-alkyl)$_2$.

The R$^2$ and R$^3$ radicals are more preferably each independently selected from $C_{3-6}$-alkyl radicals, O—($C_{3-4}$-alkyl), S—($C_{3-4}$-alkyl), N($C_{3-4}$-alkyl)$_2$.

Dialkylaminoacrylic acid derivatives preferred in connection with the present invention are shown in the following formulae (II-a) to (II-e).

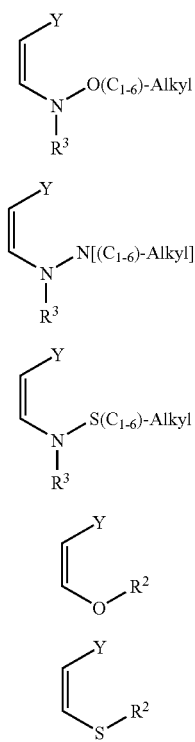

The Y group is selected from carboxylic ester groups ((C=O)OR⁶), nitrile groups (CN) and amide groups ((C=O)NR⁷R⁸); in these formulae, $R^6$, $R^7$ and $R^8$ are each independently selected from $C_{1-12}$-alkyl radicals, $C_{5-18}$-aryl or $C_{7-19}$-arylalkyl radicals; preferably from $C_{2-8}$-alkyl radicals, more preferably from $C_{3-6}$-alkyl radicals.

Examples of acrylic esters suitable in accordance with the invention are methoxyacrylic esters, alkylthioacrylic esters, methyl 3-(N,N-dimethylamino)acrylate, ethyl 3-(N,N-dimethylamino)acrylate, ethyl 3-(N,N-diethylamino)acrylate, 3-(N,N-dimethylamino)acrylonitrile, N',N'-dimethyl-3-(N,N-dimethylamino)acrylamide and N',N'-diethyl-3-(N,N-dimethylamino)acrylamide, particular preference being given to ethyl 3-(N,N-diethylamino)acrylate.

Processes for preparing dialkylaminoacrylic esters have been described before in the prior art, for example in EP-A-0 608 725.

Processes for preparing dialkylaminoacrylonitriles have been described in the prior art, for example by Rene et al in Synthesis (1986), (5), 419-420.

The acrylic acid derivatives can, if necessary, be purified, for example by distillation. However, this is generally not required in connection with the inventive reaction.

α-Fluoroamines

The α-fluoroamines used in accordance with the present invention are compounds of the general formula (III)

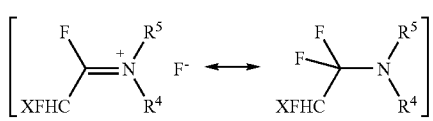

(III)

in which $R^4$ is selected from $C_{1-12}$-alkyl radicals, $C_{5-18}$-aryl or $C_{7-19}$-arylalkyl radicals, preferably from $C_{2-8}$-alkyl radicals, more preferably from $C_{3-6}$-alkyl radicals.

$R^5$, independently of $R^4$, is selected from $C_{1-12}$-alkyl radicals, $C_{5-18}$-aryl or $C_{7-19}$-arylalkyl radicals, preferably from $C_{2-8}$-alkyl radicals, more preferably from $C_{3-6}$-alkyl radicals.

X is $CF_3$, F or Cl.

The compounds are obtainable according to Petrov et al. in Journal of Fluorine Chemistry 109 (2001) 25-31 and Dmowski et al. in Chemistry of Organic Fluorine Compounds II, A Critical Review, ACS, Washington D.C. (1995) 263 by reacting fluorinated/halogenated alkenes with secondary amines and are sold commercially, for example, by DuPont.

The α-fluoroamines used with preference according to the present invention are, for example, selected from the group consisting of 1,1,2,2-tetrafluoroethyl-N,N-dimethylamine, 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoro-methyl)ethyl-N,N-diethylamine (Ishikawa reagent), 1,1,2-trifluoro-2-chloroethyl-N,N-dimethylamine and 1,1,2-trifluoro-2-chloroethyl-N,N-diethylamine (Yarovenko reagent), preference being given to 1,1,2,2-tetrafluoroethyl-N,N-dimethylamine and 1,1,2,2-tetrafluoroethyl-N,N-diethylamine and particular preference to 1,1,2,2-tetrafluoroethyl-N,N-dimethylamine.

Lewis Acids

The α-fluoroamines described above react in the presence of Lewis acids (Z) to give immonium salts, as described by Wakselman et al in J.C.S. Chem. Comm. 565 (1975) 956.

The α-fluoroamines are reacted with the Lewis acids preferably at temperatures of −80 to 50° C., preferably of −40 to 40° C., more preferably of 0 to 30° C.

Optionally, the addition of a Lewis acid can be dispensed with.

The reaction can be performed in bulk or in a solvent. Preference is given to performing the reaction in a solvent. Suitable solvents are, for example, selected from the group consisting of aliphatic and aromatic hydrocarbons, for example n-hexane, benzene or toluene, which may be substituted by fluorine and chlorine atoms, such as methylene chloride, dichloromethane, trichloromethane, carbon tetrachloride, fluorobenzene, chlorobenzene or dichlorobenzene; ethers, for example diethyl ether, diphenyl ether, methyl tert-butyl ether, isopropyl ethyl ether, dioxane, diglyme, dimethyl glycol or THF; nitriles such as methylnitrile, butylnitrile or phenylnitrile, particular preference being given to dichloromethane and acetonitrile.

Suitable Lewis acids are, for example, compounds which are selected from the group consisting of $BF_3$, $AlCl_3$, $AlF_3$, $ZnCl_2$, $PF_5$, $SbF_5$, $SnCl_4$, $BiCl_3$, $GaCl_3$, $SiCl_4$.

The Lewis acid and the α-fluoroamine are preferably used in equimolar amounts. Alternatively, the Lewis acid can also be used in excess. The ratio of Lewis acid:α-fluoroamine is, in accordance with the invention, between 1:1 and 10:1, preferably between 1:1 and 5:1, more preferably between 1:1 and 1:1.3.

In a preferred embodiment of the process according to the invention, the α-fluoroamine is initially charged in bulk or dissolved in a suitable solvent and admixed gradually with the Lewis acid.

Owing to the hydrolysis sensitivity of the α-fluoroamines, the reaction of the α-fluoroamine with the Lewis acid should be performed in anhydrous apparatus under inert gas atmosphere.

The resulting vinamidinium salts of the formula (IV) are, in contrast, neither hygroscopic nor hydrolysis-sensitive and can therefore be handled and stored under air.

The further reaction of the immonium salts with the dialkylaminoacrylic esters of the formula (II) is effected preferably without preceding isolation of the immonium salts. In a further inventive embodiment, the immonium salts can be isolated beforehand and be used as required.

The reaction of the immonium salts with the acrylic acid derivatives of the formula (II) to give the vinamidinium salts of the formula (IV)

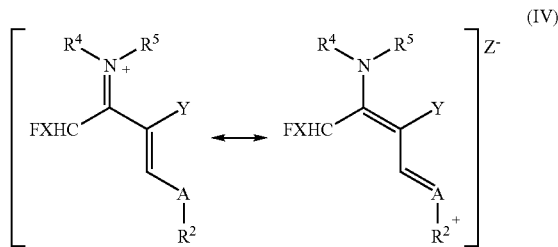

(IV)

where the anion $Z^-$ may, for example, be selected from the group consisting of $[BF_4]^-$, $[AlCl_3F]^-$, $[AlF_4]^-$, $[ZnCl_2F]^-$; $[SbF_6]^-$, $[SnCl_4F]^-$, $[BiCl_3F]^-$, $[GaCl_3F]^-$, $[ZnCl_2F]^-$, $[SnCl_4F]^-$, $[BiCl_3F]^-$, $[GaCl_3F]^-$, $[SiCl_4F]^-$, can be effected at temperatures of −40 to 60° C., preferably of −20 to 40° C., more preferably of 0 to 50° C.

The immonium salts and the acrylic acid derivatives are preferably used in equimolar amounts. Alternatively, the immonium salts or the acrylic acid derivatives can also be used in excess. The ratio of immonium salt:acrylic acid derivative is, in accordance with the invention, between 1:10 and 10:1, preferably between 1:5 and 5:1, more preferably between 1.3:1 and 1:1.3.

The solvents used are preferably those solvents which have also been used beforehand for the synthesis of the immonium salt.

In a preferred embodiment of the process according to the invention, the immonium salt is initially charged in bulk or dissolved in a suitable solvent and admixed gradually with the acrylic acid derivatives.

In a further embodiment of the process according to the invention, acrylic acid derivatives (II) and α-fluoroamines (III) are optionally initially charged in a solvent and admixed gradually with the Lewis acid. Finally, a hydrazine of the formula (V) is then added.

The immonium salts of the formula (IV) can be isolated by simple removal of the solvent.

However, the immonium salts of the formula (IV) are preferably reacted without preceding isolation with hydrazines of the general formula (V), preferably with methylhydrazine, to give 3-dihalomethylpyrazole-4-carboxylic esters of the formula (I).

Very particular preference is given to using hydrazine, methylhydrazine and ethylhydrazine, even greater preference being given to methylhydrazine.

Preferred compounds of the general formula (I) include:
Methyl 1-methyl-3-difluoromethyl-4-pyrazolecarboxylate, ethyl 1-methyl-3-difluoromethyl-4-pyrazole-carboxylate, ethyl 1-methyl-3-chlorofluoromethyl-4-pyrazolecarboxylate, ethyl 1-methyl-3-chlorofluoromethyl-4-pyrazolecarboxylate, methyl 1-methyl-3-(trifluoromethyl)fluoromethyl-4-pyrazolecarboxylate, ethyl 1-methyl-3-(trifluoromethyl)fluoromethyl-4-pyrazolecarboxylate, particular preference being given to ethyl 1-methyl-3-difluoromethyl-4-pyrazolecarboxylate and methyl 1-methyl-3-difluoromethyl-4-pyrazolecarboxylate.

Preference is given to performing the reaction of the immonium salts of the formula (IV) with the hydrazines of the formula (V) in the presence of solvents. Suitable solvents are, for example, those which have also been specified for the performance of the preceding steps.

The reaction with the alkylhydrazines can be effected, for example and with preference, at −30 to +80° C., more preferably at −20 to +25° C. and most preferably at −10 to +40° C.

For reasons of economic viability, preference is given to performance at room temperature (RT).

It may be found in a particularly advantageous manner that the formation of the 3-halo-alkyl-4-pyrazolecarboxylic acid derivatives proceeds with high regioselectivity even at room temperature.

The regioisomeric 4-haloalkyl-3-pyrazolecarboxylic acid derivatives formed in a low proportion (≦8%) can be removed from the desired products owing to their different physical properties by suitable processes, for example distillation or crystallization, or by simple washing with, for example, cyclohexanes.

It should also be mentioned as advantageous that all reaction steps of the process according to the invention can be performed one after another without intermediate purification/isolation of the intermediates.

The 3-haloalkyl-4-pyrazolecarboxylic acid derivatives of the formula (I) can optionally be converted in a manner known per se (Houben-Weyl, Methoden der organischen Chemie [Methods of organic chemistry], 4th edition, volume E5, p. 223ff.), for example by acidic or alkaline hydrolysis, to 3-haloalkyl-4-pyrazolecarboxylic acids.

Preference is given to alkaline hydrolysis. This can be effected in a manner known per se, for example, by reaction with bases, for example alkali metal hydroxides, for example lithium hydroxide, sodium hydroxide or potassium hydroxide or aqueous solutions thereof. Examples of suitable solvents include water, alcohols, for example methanol, ethanol and isopropanol, aromatic hydrocarbons, for example toluene, acetone, pyridine or mixtures of such solvents.

3-Haloalkyl-4-pyrazolecarboxylic acids preferred in connection with the present invention are 1-methyl-3-difluoromethyl-4-pyrazolecarboxylic acid, 1-methyl-3-chlorofluoromethyl-4-pyrazolecarboxylic acid, 1-methyl-3-(trifluoromethyl)fluoromethyl-4-pyrazolecarboxylic acid, 3-difluoromethyl-4-pyrazolecarboxylic acid, 3-(trifluoromethyl)fluoromethyl-4-pyrazolecarboxylic acid and 3-chlorofluoromethyl-4-pyrazolecarboxylic acid, particular preference being given to 1-methyl-3-difluoromethyl-4-pyrazolecarboxylic acid.

The invention will be illustrated in detail with reference to the examples which follow, but without restricting it to them.

EXAMPLES

Example 1

N-[(2E)-1-(difluoromethyl)-3-(dimethylamino)-2-(ethoxycarbonyl)prop-2-en-1-ylidene]-N-methyl-methanaminium tetrafluoroborate

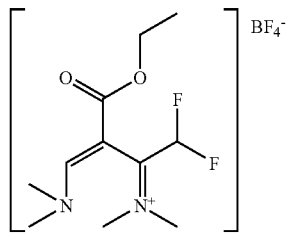

8.8 g (60 mmol) of N-1,1,2,2-tetrafluoroethyldimethylamine were initially charged in 50 ml of dichloromethane under argon, and 8.2 g (60 mmol) of boron trifluoride-diethyl ether complex were added at RT. The mixture was stirred for 30 min and then admixed with 7.15 g (50 mmol) of ethyl dimethylaminoacrylate. After stirring at RT for 2 h and removing the dichloromethane under reduced pressure, 12.4 g of the product (100% yield) were obtained as a yellow oil.

$^{19}$F NMR (CDCl$_3$) δ=−120.35, (d, 2F, J=51 Hz); −151.2 (s, 4F) ppm.

$^1$H NMR (CDCl$_3$) δ=1.25 (t, 3H); 2.8, (s, 6H); 3.45 (m, 6H); 4.2 (qu, CH$_2$); 6.87 (t, 1H); 8.16 (s, 1H) ppm.

Example 2

N-[(2E)-1-(Chlorofluoromethyl)-3-(dimethylamino)-2-(ethoxycarbonyl)-prop-2-en-1-ylidene]-N-methyl-methanaminium tetrafluoroborate

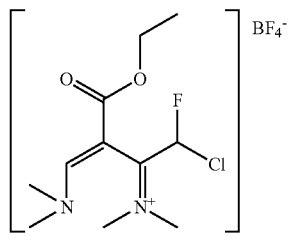

17.6 g (0.1 mmol) of N-1,1,2-trifluoro-2-chloroethyldimethylamine were initially charged in 100 ml of dichloromethane under argon and admixed at RT with 13.6 g (0.1 mol) of boron trifluoride-diethyl ether complex. After stirring for 30 min, 14.3 g (0.1 mol) of ethyl dimethylaminoacrylate were added and the mixture was stirred at RT for 2 h. After the dichloromethane had been removed under reduced pressure, 25.2 g (95% of theory) of the product were obtained.

Example 3

Ethyl 3-(difluoromethyl)-1-methyl-1H-pyrazole-4-carboxylate

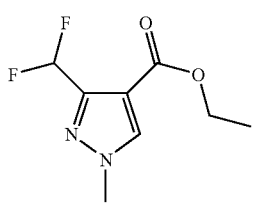

10.0 g (30 mmol) of N-[(2E)-1-(difluoromethyl)-3-(dimethylamino)-2-(ethoxycarbonyl)prop-2-en-1-ylidene]-N-methylmethanaminium tetrafluoroborate were dissolved in 50 ml of acetonitrile and admixed with 2.3 g of methylhydrazine. After stirring at RT for 2 h, the acetonitrile was removed completely under reduced pressure. Distillation under reduced pressure or crystallization from n-hexane afforded 5.3 g (86% of theory) of the product having an m.p. of 63-65° C.

$^{19}$F NMR (CDCl$_3$): δ=−117.2 (d) ppm.

$^1$H NMR (CDCl$_3$): δ=1.35 (t, 3H); 3.96 (s, 3H); 4.31 (qu, 2H); 7.10 (t, 1H); 8.15 (s, 1H) ppm.

Example 4

Ethyl 3-(chlorofluoromethyl)-1-methyl-1H-pyrazole-4-carboxylate

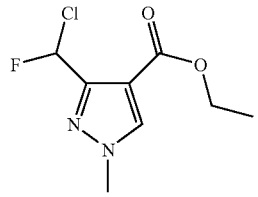

In a departure from Example 3, N-[(2E)-1-(difluoromethyl)-3-(dimethylamino)-2-(ethoxycarbonyl)prop-2-en-1-ylidene]-N-methylmethanaminium tetrafluoroborate is used.

$^{19}$F NMR (CDCl$_3$): δ=−133.8 (d, J=47.5) ppm.

Example 5

Ethyl 3-(1,2,2,2-tetrafluoroethyl)-1-methyl-1H-pyrazole-4-carboxylate

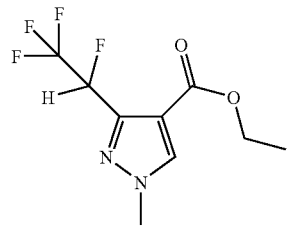

25.3 g (0.1 mmol) of N,N-diethyl-1,1,2,3,3,3-hexafluoropropylamine were initially charged in 100 ml of dichloromethane under argon and admixed at RT with 13.6 (0.1 mol) of boron trifluoride-diethyl ether complex. After stirring for 30 min, 14.3 g (0.1 mmol) of ethyl dimethylaminoacrylate were added and the mixture was stirred at RT for 2 h. After the dichloromethane had been removed under reduced pressure, approx. 35 g of the vinamidinium salt were obtained. 5.6 g of methylhydrazine were initially charged in 40 ml of acetonitrile and the solution of vinamidinium salt in 30 ml of acetonitrile was added at 10° C.

After stirring at RT for 2 h, the acetonitrile was removed completely under reduced pressure. 20 g (82%) of the product were isolated as an oil by chromatography on SiO$_2$.

$^{19}$F NMR (CDCl$_3$): δ=−76.8 (dd., 3F), −191.86 (d. qw, 1F)-ppm.

$^1$H NMR (CDCl$_3$): δ=1.35 (t, 3H); 3.96 (s, 3H); 4.35 (qu, 2H); 6.52 (d, qu, 1H), 8.10 (s, 1H) ppm.

Example 6

N-[(2E)-1-(difluoromethyl)-3-methoxy-2-(methoxycarbonyl)prop-2-en-1-ylidene]-N-methyl-methanaminium tetrafluoroborate

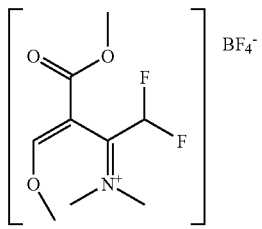

8.7 g (60 mmol) of N-1,1,2,2-tetrafluoroethyldimethylamine were initially charged in 50 ml of dichloromethane under argon, and 8.2 g (60 mmol) of boron trifluoride-diethyl ether complex were added at RT. The mixture was stirred for 30 min and then admixed with 6.38 g (55 mmol) of methyl methoxyacrylate. After stirring at RT for 2 h and removing the dichloromethane under reduced pressure, 12.4 g of the product (100% yield) were obtained as a yellow oil.

$^{19}$F NMR (CDCl$_3$) δ=−121.55, (d, 2F, J=51 Hz); −150.2 (s, 4F) ppm.

Example 7

Methyl 3-(difluoromethyl)-1-methyl-1H-pyrazole-4-carboxylate

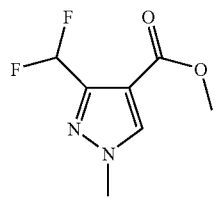

The procedure of Example 2 is repeated, except that N-[(2E)-1-(difluoromethyl)-3-methoxy-2-(methoxy-carbonyl)prop-2-en-1-yliden]-N-methylmethanaminium tetrafluoroborate is employed.

The product is isolated as a yellow oil by means of chromatography on SiO$_2$ $^{19}$F NMR (CDCl$_3$): δ=−117.5 (d) ppm.

Example 8

Ethyl 3-(difluoromethyl)-1-methyl-1H-pyrazole-4-carboxylate (one-pot process)

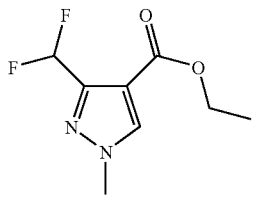

10.8 g of N-1,1,2,2-tetrafluoroethyldimethylamine were initially charged in 50 ml of acetonitrile under argon and 26 g of boron trifluoride as a 17% solution in CH$_3$CN were added at RT. The mixture was stirred for 30 min and then admixed with 8.67 g of ethyl dimethylaminoacrylate. The mixture was stirred at RT for 2 h and then added slowly to the solution of 3.4 g of methylhydrazine in 10 ml of acetonitrile at 10° C. After stirring at RT for 2 h, the acetonitrile was removed completely under reduced pressure and the product was admixed with water and filtered off. Distillation under reduced pressure or washing with cyclohexane afforded 10 g of the product with the purity of 99% and an m.p. of 62-63° C.

The invention claimed is:

1. A process for preparing a 3-dihalomethylpyrazole-4-carboxylic acid derivative of formula (I)

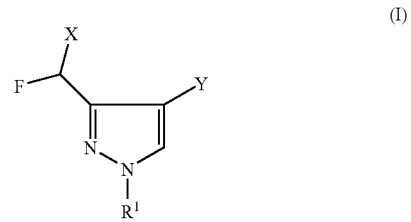

in which

R$^1$ is selected from C$_{1-12}$-alkyl radicals, and C$_{5-18}$-aryl or C$_{7-19}$-arylalkyl radicals, Y is selected from (C=O)OR$^6$, CN and (C=O)NR$^7$R$^8$, where R$^6$, R$^7$ and R$^8$ are each independently selected from C$_{1-12}$-alkyl radicals, and C$_{5-18}$-aryl or C$_{7-19}$-arylalkyl radicals; and X is F, Cl or CF$_3$ comprising reacting an α-fluoroamine of formula (III)

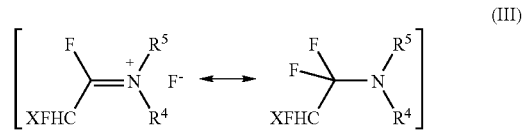

in which

R$^4$ is selected from C$_{1-12}$-alkyl radicals, and C$_{5-18}$-aryl or C$_{7-19}$-arylalkyl radicals, R$^5$, independently of R$^4$, is selected from C$_{1-12}$-alkyl radicals, C$_{5-18}$-aryl and/or C$_{7-19}$-arylalkyl radicals, and X is F, Cl or CF$_3$, in the presence of a Lewis acid (Z) with an acrylic acid derivative of formula (II)

in which

A is selected from O, S and NR$^3$,

Y is selected from (C=O)OR$^6$, CN and (C=O)NR$^7$R$^8$, where R$^6$, R$^7$ and R$^8$ are each independently selected from C$_{1-12}$-alkyl radicals, and C$_{5-18}$-aryl or C$_{7-19}$-arylalkyl radicals; and R$^2$ and R$^3$ are each independently selected from C$_{1-12}$-alkyl radicals, C$_{5-18}$-aryl; C$_{7-19}$-aryl-alkyl radicals, —OR', —SR', and —NR'$_2$, where R' may be a (C$_1$-C$_5$) alkyl radical, or R$^2$ and R$^3$, together with the nitrogen atom to which they are bonded, may form a five- or six-membered ring, to give a vinamidinium salt of formula (IV)

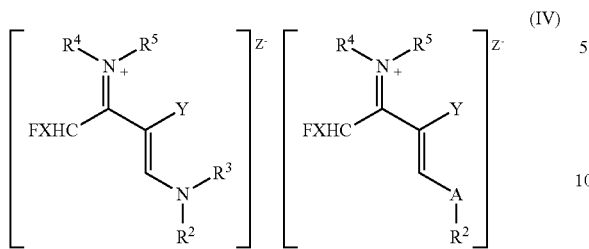

in which Z⁻ is an anion;
and subsequent reaction thereof with an alkylhydrazine of formula (V)

2. A Process for preparing a 3-dihalomethylpyrazole-4-carboxylic acid derivative of formula (I)

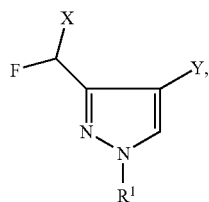

in which
$R^1$ is selected from hydrogen, $C_{1-12}$-alkyl radicals, and $C_{5-18}$-aryl or $C_{7-19}$-arylalkyl radicals,
Y is selected from (C=O)$OR^6$, CN and (C=O)$NR^7R^8$, where $R^6$, $R^7$ and $R^8$ are each independently selected from $C_{1-12}$-alkyl radicals, and $C_{5-18}$-aryl or $C_{7-19}$-arylalkyl radicals; and
X is F, Cl or $CF_3$
comprising reacting an α-fluoroamine of formula (III)

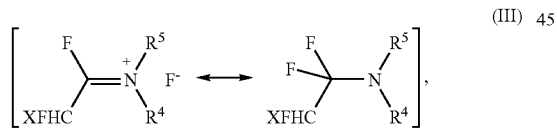

in which
$R^4$ is selected from $C_{1-12}$-alkyl radicals, and $C_{5-18}$-aryl or $C_{7-19}$-arylalkyl radicals,
$R^5$, independently of $R^4$, is selected from $C_{1-12}$-alkyl radicals, and $C_{5-18}$-aryl or $C_{7-19}$-arylalkyl radicals, and
X is F, Cl or $CF_3$,
with an acrylic acid derivative of formula (II)

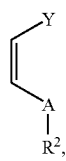

in which
A is selected from O, S and $NR^3$,
Y is selected from (C=O)$OR^6$, CN and (C=O)$NR^7R^8$, where $R^6$, $R^7$ and $R^8$ are each independently selected from $C_{1-12}$-alkyl radicals, and $C_{5-18}$-aryl or $C_{7-19}$-arylalkyl radicals; and
$R^2$ and $R^3$ are each independently selected from $C_{1-12}$-alkyl radicals, $C_{5-18}$-aryl or $C_{7-19}$-aryl-alkyl radicals, —OR', —SR', and —NR'₂, where R' may be a ($C_1$-$C_5$) alkyl radical,
or $R^2$ and $R^3$, together with the nitrogen atom to which they are bonded, may form a five- or six-membered ring,
and subsequent reaction thereof with a hydrazine of formula (V)

3. A Process according to claim 1, wherein the anion Z⁻ is selected from the group consisting of [$BF_4$]⁻, [$AlCl_4$]⁻, [$AlF_4$]⁻, [$ZnCl_3$]⁻, [$PF_6$]⁻, [$SbF_6$]⁻, [$SnCl_5$]⁻, [$BiCl_4$]⁻, and [$GaCl_4$]⁻.

4. A Process according to claim 1 wherein Y is a carboxylic ester group of the formula (C=O)$OR^6$ where $R^6$ is selected from $C_{1-12}$-alkyl radicals, and $C_{5-18}$-aryl or $C_{7-19}$-aryl-alkyl radicals.

5. A Process according to claim 1, wherein all reaction steps are performed without intermediate purification/isolation of an intermediate.

6. A Vinamidinium salt of formula (IV)

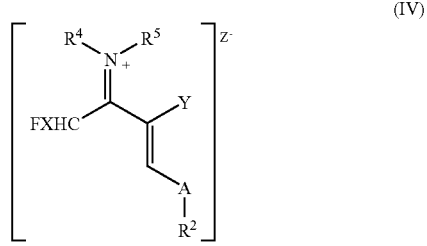

in which
$R^1$ is selected from $C_{1-12}$-alkyl radicals, and $C_{5-18}$-aryl or $C_{7-19}$-arylalkyl radicals,
Y is selected from (C=O)$OR^6$, CN and (C=O)$NR^7R^8$, where $R^6$, $R^7$ and $R^8$ are each independently selected from $C_{1-12}$-alkyl radicals, and $C_{5-18}$-aryl or $C_{7-19}$-arylalkyl radicals; and
X is F, Cl or $CF_3$
$R^4$ is selected from $C_{1-12}$-alkyl radicals, and $C_{5-18}$-aryl or $C_{7-19}$-arylalkyl radicals,
$R^5$, independently of $R^4$, is selected from $C_{1-12}$-alkyl radicals, and $C_{5-18}$-aryl or $C_{7-19}$-arylalkyl radicals, and
Z⁻ is an anion.

7. Vinamidinium salt according to claim 6, where X=F.

8. A Vinamidinium salt according to claim 6 wherein Y is a carboxylic ester group of formula (C=O)$OR^6$ where $R^6$ is selected from $C_{1-12}$-alkyl radicals, and $C_{5-18}$-aryl or $C_{7-19}$-arylalkyl radicals.

9. A Vinamidinium salt according to claim 6 wherein Z⁻ is selected from the group consisting of [$BF_4$]⁻, [$AlCl_4$]⁻, [$AlF_4$]⁻, [$ZnCl_3$]⁻, [$PF_6$]⁻, [$SbF_6$]⁻, [$SnCl_5$]⁻, [$BiCl_4$]⁻, and [$GaCl_4$]⁻.

10. Compound of the formula (VI)
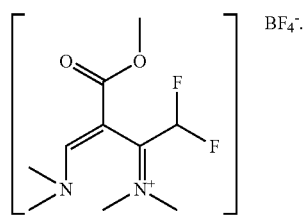
(VI)
11. Compound of the formula (VII)
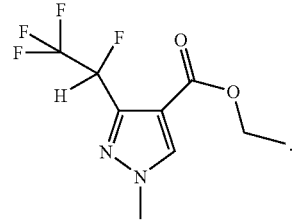
(VII)
* * * * *